United States Patent
Yang et al.

(10) Patent No.: US 12,383,397 B2
(45) Date of Patent: Aug. 12, 2025

(54) PROSTHETIC HEART VALVE WITH SUTURE LOOP PREVENTING MEMBER

(71) Applicant: Edwards Lifesciences Corporation, Irvine, CA (US)

(72) Inventors: Yimin Yang, Irvine, CA (US); Michael Quach, Long Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1013 days.

(21) Appl. No.: 17/395,341

(22) Filed: Aug. 5, 2021

(65) Prior Publication Data
US 2021/0361423 A1 Nov. 25, 2021

Related U.S. Application Data

(63) Continuation of application No. PCT/US2020/015798, filed on Jan. 30, 2020.
(Continued)

(51) Int. Cl.
*A61F 2/24* (2006.01)

(52) U.S. Cl.
CPC .... *A61F 2/2418* (2013.01); *A61F 2210/0014* (2013.01); *A61F 2220/0075* (2013.01);
(Continued)

(58) Field of Classification Search
CPC ............ A61F 2/2418; A61F 2210/0014; A61F 2220/0075; A61F 2230/0091; A61F 2250/0087
See application file for complete search history.

(56) References Cited

U.S. PATENT DOCUMENTS 3,143,742 A 8/1964 Cromie
3,320,972 A 5/1967 High et al.
(Continued)

FOREIGN PATENT DOCUMENTS

EP 0125393 A1 11/1984
EP 0143246 A2 6/1985
(Continued)

OTHER PUBLICATIONS

Bapat, Vinayak et al. "A Guide to Fluoroscopic Identification and Design of Bioprosthetic Valves: A Reference for Valve-in-Valve Procedure", Wiley Periodicals, Inc., 2012.

*Primary Examiner* — Jerrah Edwards
*Assistant Examiner* — Aren Patel
(74) *Attorney, Agent, or Firm* — Guy Cumberbatch

(57) ABSTRACT

A prosthetic heart valve system includes a prosthetic heart valve having an inflow side, and an outflow side. The heart valve further includes a base at the inflow side, a plurality of commissure posts and valve leaflets secured to the commissure posts to permit flow through the heart valve. An anti-loop member has a first portion on the inflow side of the heart valve and a second portion on the outflow side of the heart valve. The second portion of the anti-loop member is arranged along each commissure post at the tip of each commissure post, and arranged along at least one commissure post twice to form a loop around all of the commissure posts. The anti-loop member is made of a material sufficiently flexible to be removed from the commissure posts without damaging the heart valve yet rigid enough to retain its shape when coming in contact with sutures.

20 Claims, 16 Drawing Sheets

Related U.S. Application Data

(60) Provisional application No. 62/801,598, filed on Feb. 5, 2019.

(52) U.S. Cl.
CPC ............... *A61F 2230/0091* (2013.01); *A61F 2250/0087* (2013.01)

(56) References Cited

U.S. PATENT DOCUMENTS

| | | |
|---|---|---|
| 3,371,352 A | 3/1968 | Siposs et al. |
| 3,546,710 A | 12/1970 | Ivanovich et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson et al. |
| 5,895,420 A | 4/1999 | Mirsch et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson et al. |
| 6,168,614 B1 | 1/2001 | Andersen et al. |
| 6,176,877 B1 | 1/2001 | Buchanan et al. |
| 6,197,054 B1 | 3/2001 | Hamblin et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson et al. |
| 6,409,674 B1 | 6/2002 | Brockway et al. |
| 6,425,916 B1 | 7/2002 | Garrison et al. |

(56) References Cited

U.S. PATENT DOCUMENTS

| | | |
|---|---|---|
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,529,474 B2 | 9/2013 | Gupta et al. |
| 8,622,936 B2 | 1/2014 | Schenberger et al. |
| 9,101,264 B2 | 8/2015 | Acquista |
| 9,101,281 B2 | 8/2015 | Reinert et al. |
| 9,693,862 B2 | 7/2017 | Campbell et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0082686 A1* | 6/2002 | Nguyen-Thien-Nhon ............... A61F 2/2427 623/2.11 |
| 2002/0123802 A1 | 9/2002 | Snyders |
| 2002/0138138 A1 | 9/2002 | Yang |
| 2002/0151961 A1* | 10/2002 | Lashinski ............ A61F 2/2451 623/2.11 |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0148017 A1* | 7/2004 | Stobie .................. A61F 2/2427 623/2.11 |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |

(56) References Cited

U.S. PATENT DOCUMENTS

| | | |
|---|---|---|
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195183 A1* | 8/2006 | Navia ............... A61F 2/2418 623/2.11 |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192591 A1 | 7/2009 | Ryan et al. |
| 2009/0192599 A1 | 7/2009 | Lane et al. |
| 2010/0049313 A1 | 2/2010 | Alon et al. |
| 2010/0145438 A1 | 6/2010 | Barone |
| 2010/0256723 A1 | 10/2010 | Murray |
| 2012/0123284 A1 | 5/2012 | Kheradvar |
| 2012/0296382 A1 | 11/2012 | Shuros et al. |
| 2013/0144379 A1 | 6/2013 | Najafi et al. |
| 2014/0039609 A1* | 2/2014 | Campbell ............. A61F 2/2412 623/2.11 |
| 2014/0128964 A1 | 5/2014 | Delaloye |
| 2014/0188221 A1 | 7/2014 | Chung et al. |
| 2014/0364707 A1 | 12/2014 | Kintz et al. |
| 2015/0045635 A1 | 2/2015 | Tankiewicz et al. |
| 2016/0045316 A1 | 2/2016 | Braido et al. |
| 2016/0235525 A1* | 8/2016 | Rothstein ............. A61F 2/2418 |
| 2017/0224486 A1* | 8/2017 | Delaloye ................ A61F 2/966 |
| 2019/0224009 A1* | 7/2019 | Conklin ................ A61F 2/2427 |
| 2019/0321170 A1 | 10/2019 | Green et al. |
| 2021/0113330 A1* | 4/2021 | Benichou ............. A61F 2/2418 |

FOREIGN PATENT DOCUMENTS

| | | |
|---|---|---|
| SU | 1116573 A | 7/1985 |
| SU | 1697790 A1 | 12/1991 |
| WO | 1992013502 A1 | 8/1992 |
| WO | 1997042871 A1 | 11/1997 |

* cited by examiner

PROSTHETIC HEART VALVE WITH SUTURE LOOP PREVENTING MEMBER

CROSS-REFERENCE TO RELATED APPLICATION

This application is a continuation of PCT Application PCT/US20/15798, filed Jan. 30, 2020, which claims the benefit of U.S. Application No. 62/801,598, filed Feb. 5, 2019, which is incorporated by reference in its entirety for all purposes.

FIELD

The present disclosure generally concerns medical devices, deployment mechanisms, and methods for deploying such medical devices. More specifically, the disclosure relates to the surgical replacement of heart valves that have malformations and/or dysfunctions. Some embodiments relate to a prosthetic heart valve system having an anti-looping device to prevent suture looping during deployment of the prosthetic heart valve to the native heart valve site, for example for a mitral valve replacement procedure. Some embodiments also relate to methods of using the anti-looping device to facilitate implantation of prosthetic heart valves.

BACKGROUND

Referring first to FIG. 1, the human heart is generally separated into four pumping chambers which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary arteries to the lungs to again supply the blood with oxygen.

Each of the valves associated with the chambers of the heart are one-way valves that have leaflets to control the directional flow of the blood through the heart and to prevent backflow of the blood into other chambers or blood vessels that are upstream of the particular chamber. The valves are each supported by an annulus having a dense fibrous ring attached either directly or indirectly to the atrial or ventricular muscle fibers.

When a valve becomes diseased or damaged, the efficiency and/or general functionality of the heart may be compromised. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques can be performed to replace a diseased or damaged valve. For example, the leaflets of a diseased or damaged native valve may be at least partially removed to prepare the valve annulus for receiving a prosthetic replacement valve. FIG. 2 shows an example of one type of popular prosthetic replacement valve 1 that is a tissue-type bioprosthetic valve generally constructed with natural-tissue valve leaflets 2, made for example, from porcine tissue or bovine pericardium, or from synthetic or semisynthetic material, that are mounted on a surrounding valve stent structure or frame 3. The shape and structure of the leaflets 2 are supported by a number of commissure posts 4 positioned circumferentially around the valve stent structure 3. In these valves, a biocompatible cloth-covered suture or sewing ring 5 can also be provided on an inflow end of the stent structure 3 of the valve 1, to facilitate easier attachment to the native valve annulus. Such prosthetic valves function much like natural human heart valves, where the leaflets coapt against one another to effect the one-way flow of blood.

When implanting a tissue type prosthetic valve as described above at a native valve annulus, a number of sutures may be involved in the attachment process, many of which may be pre-installed for providing a track on which the valve is advanced, or "parachuted," until it is properly positioned at the implant site. Additional sutures may also be tied and knotted between the prosthetic valve and the heart walls after proper placement, to securely attach or hold the valve implant in place.

Depending on the direction of implantation, for example with some mitral valve replacement procedures, commissure posts of the stent or frame, or other portions of the prosthetic valve, may be pointed distally and advanced on a blind side of the valve, thereby obstructing visibility of the posts or other portions during advancement and implantation. Such procedures can also require a prosthetic valve and its holder to fit through an incision of approximately 15-20 mm in its narrowest direction or dimension. Meanwhile, in some cases, the prosthetic valves are implanted through small access channels using one of various minimally invasive surgical procedures, where visibility at the implant site may be impeded or obstructed.

Each of the above factors may lead to tangling of the sutures with the valve prosthesis, most commonly with the commissure posts of the frame, since the commissure posts provide a protrusion on which the sutures can easily loop around and tangle. This type of entanglement of sutures with prosthetic valves is referred to as "suture looping," which specifically refers to instances where a suture is inadvertently wrapped around one or more of the commissure post tips, where it can then migrate towards and damage the leaflets or interfere with proper leaflet coaptation or other valve operation when the sutures are tightened or secured, resulting in improper valve operation.

An example of suture looping is shown in FIGS. 3A-3C. With reference to FIG. 3A, a prosthetic mitral valve 10 is shown as it is parachuted to a mitral valve opening 12 defined by a valve annulus 14 of the heart. One pre-installed suture 16 is shown that has been threaded through a sewing ring 18 of the valve 10, down to the valve annulus 14 and back up through the sewing ring. Several sutures are used to parachute the valve and secure the valve to the annulus. Only one suture is shown in this example for clarity.

With reference to FIG. 3B, an example of tangling is shown where a commissure post 20 passes between the left strand 22 and the right strand 24 of the suture 16. As the heart valve 10 continues to move down the strands and into the valve opening 12, the right strand 24 gets looped behind the commissure post 20 while the left strand 22 remains in front. To complete the procedure, the heart valve is pushed down until the sewing ring 18 contacts the valve annulus 14. But this final action will cause the right strand 24 to slide along the inside of the commissure post 20 away from the tip and push on the flexible valve leaflets 26 (FIG. 3C), potentially causing damage or affecting blood flow through the valve. FIG. 3C is a view from the opposite side of the valve opening 12 showing the right strand 24 looped around the commissure post 20 and pushing down on the valve leaflets 26. Such tangling may not be apparent to the surgical team at the time of implantation, and will only be revealed some time later when valve operation is observed to be improper or other complications arise in the patient, in which case it may be necessary to initiate another procedure to repair or replace the prosthetic valve.

Attempts have been made to resolve the problem of suture looping, some of which revolve around the holders which hold the prosthetic valves when they are delivered to the native valve annulus. In one example, a holder has a mechanism that urges the commissure posts of the prosthetic valve radially inward during delivery, so that the ends of the commissure posts are pointed inwards, to reduce the possibility of sutures catching against or looping around them. After the valve prosthesis is delivered to the implant site, the holder is removed, releasing and expanding the commissure posts to their original positions. However, although the commissure posts are biased inwardly during delivery, since the ends of the commissure posts remain free, these holders have not been fully effective in eliminating instances of suture looping.

Another valve holder system developed for use in mitral valve replacement procedures to protect the valve from suture looping during valve implantation is described in U.S. Pat. No. 6,964,682, the contents of which are incorporated by reference herein in their entirety. The system includes monofilament deflection sutures that attach to both the holder and pairs of commissures of the prosthetic valve, so that the sutures run across the outflow end of the valve between the ends of the commissures. When the holder is actuated, a central post extends distally through the prosthetic valve between the leaflets and pushes against the sutures in the middle of the valve between the commissures, pushing the sutures distally and causing an angled tent-like or umbrella shape of sutures. The pressure on the sutures deflects the commissures slightly inward, while also forming the angled umbrella shape of the sutures that slope outwardly and downwardly from the central post to the commissure posts. These angled surfaces deflect away from the prosthetic valve any other sutures, such as the pre-installed attachment sutures, mentioned above, that might otherwise engage and be looped around a commissure or valve leaflet.

Other holders have also been developed in an attempt to further reduce instances of suture looping. However, some of these holders are very complex, for example, incorporating various rotary and advancement mechanisms in addition to the original hold and release mechanisms, such that a number of additional steps must be taken by the practitioner to operate the holders correctly. Many of these holders have proven to be too complicated and/or prone to user error, such as a failure to execute all deployment steps in the correct order. Consequently, when practitioners use these holders improperly, suture looping can still occur, while the implant process may also be further complicated by issues arising from user error.

Accordingly, there is a need for an improved prosthetic heart valve assembly that is easier to use during valve implantation, is more effective to prevent suture looping, is simpler in design, and provides improved visibility for the surgical team when implanting the valve.

SUMMARY

In a preferred embodiment, a prosthetic heart valve system includes a prosthetic heart valve having an inflow side and an outflow side, and a flow axis therethrough. The heart valve further includes a base at the inflow side, a plurality of commissure posts extending from the base away from the inflow side and circumferentially spaced around the flow axis, and valve leaflets secured to the commissure posts to permit flow through the heart valve. Each commissure post has a tip on the outflow side. An anti-loop member has a first portion on the inflow side of the heart valve and a second portion on the outflow side of the heart valve. The second portion of the anti-loop member is arranged along each commissure post at the tip of each commissure post, and arranged along at least one commissure post twice to form a loop around all of the plurality of commissure posts. The anti-loop member is preferably made of a material sufficiently flexible to be removed from the commissure posts without damaging the heart valve by pulling on the first end portion of the anti-loop member yet rigid enough to retain its shape when coming in contact with sutures used to secure the heart valve to a heart valve annulus.

In a further embodiment, the second portion of the anti-loop member is attached to each commissure post at the tip of each commissure post and to the at least one commissure post twice, to form the loop around all of the plurality of commissure posts. In addition, the anti-loop member may be attached to a side of each commissure post facing away from the flow axis. Further, the anti-loop member may loop around the plurality of commissure posts twice. In an alternative embodiment, an outer loop of the anti-loop member is attached to a side of each commissure post facing away from the flow axis and an inner loop of the anti-loop member is inside the outer loop. In another embodiment, the anti-loop member is a superelastic nitinol. Furthermore, the anti-loop member may be shape set in a coiled form. In an alternative embodiment, a free end of the second portion of the anti-loop member may be located radially inside the periphery of the plurality of commissure posts.

In another embodiment, a free end of the second portion of the anti-loop member is an enlarged portion shaped to prevent damage to surrounding tissue. The enlarged portion is in the shape of a ball.

In a preferred embodiment, the base of the prosthetic heart valve has a sewing ring to engage a native valve annulus and the anti-loop member passes through the sewing ring. Preferably, the anti-loop member passes through the sewing ring adjacent an inner diameter of the sewing ring.

Further, the anti-loop member may extend from a tip of one commissure post and through the sewing ring at a location closer to an adjacent commissure post than the one commissure post.

In another embodiment, a prosthetic heart valve system, includes a prosthetic heart valve having an inflow side and an outflow side, and a flow axis therethrough. The heart valve further includes a base at the inflow side, a plurality of commissure posts extending from the base away from the inflow side and circumferentially spaced around the flow axis, and valve leaflets secured to the commissure posts to permit flow through the heart valve. Each commissure post has a tip on the outflow side. An anti-loop member has a first portion of the anti-loop member on the inflow side of the heart valve and a second portion on the outflow side of the heart valve. The second portion of the anti-loop member is arranged along each commissure post at the tip of each commissure post, and arranged along at least one commissure post twice to form a loop around all of the plurality of commissure posts. A valve holder is also removably secured to the prosthetic heart valve. The anti-loop member is preferably made of a material sufficiently flexible to be removed from the commissure posts without damaging the heart valve by pulling on the first end portion of the anti-loop member yet rigid enough to retain its shape when coming in contact with sutures used to secure the heart valve to a heart valve annulus.

In a further embodiment, the first portion of the anti-loop member is secured to the valve holder such that removal of the valve holder from the heart valve also results in removal of the anti-loop member from the heart valve. In another embodiment, the first portion of the anti-loop member has an indicator to alert a member of the surgical team to remove the anti-loop coil. The indicator is preferably a contrasting color to the environment.

BRIEF DESCRIPTION OF THE DRAWINGS

Further features and advantages will become apparent from the description of embodiments using the accompanying drawings. In the drawings.

DETAILED DESCRIPTION

Disclosed herein are various embodiments of a prosthetic heart valve with anti-loop member for assisting in the delivery and implantation of a prosthetic heart valve at an implant site, and methods for preparing the prosthetic heart valve for such procedures. Embodiments of the prosthetic heart valve with anti-loop member herein are easy to use and simple in design.

The valve systems disclosed herein are particularly useful for avoiding suture looping during advancement of the prosthetic valve to the implant site as well as during final suturing of the valve at the native valve annulus. In procedures where commissure posts of the prosthetic valve point distally, for example in many mitral valve replacement procedures, the commissure posts point in the direction of valve advancement and may be more prone to suture looping or other entangling. In these cases, an anti-loop member according to embodiments disclosed herein deflects the pre-installed sutures away from the prosthetic valve. In some embodiments, the anti-loop member is pre-deployed without requiring any action by the surgeon or operating room staff and is ready for delivery to the native valve annulus upon removal of the packaging. Upon securement of the prosthetic heart valve to the native valve annulus, the anti-loop member can be easily removed from the heart valve without causing any damage to the valve or valve leaflets. In this fashion, ease of use can be maintained, while user error can be minimized. In addition, in some embodiments, the surgical team has improved visibility of the surgical site during the procedure.

Figure 1:
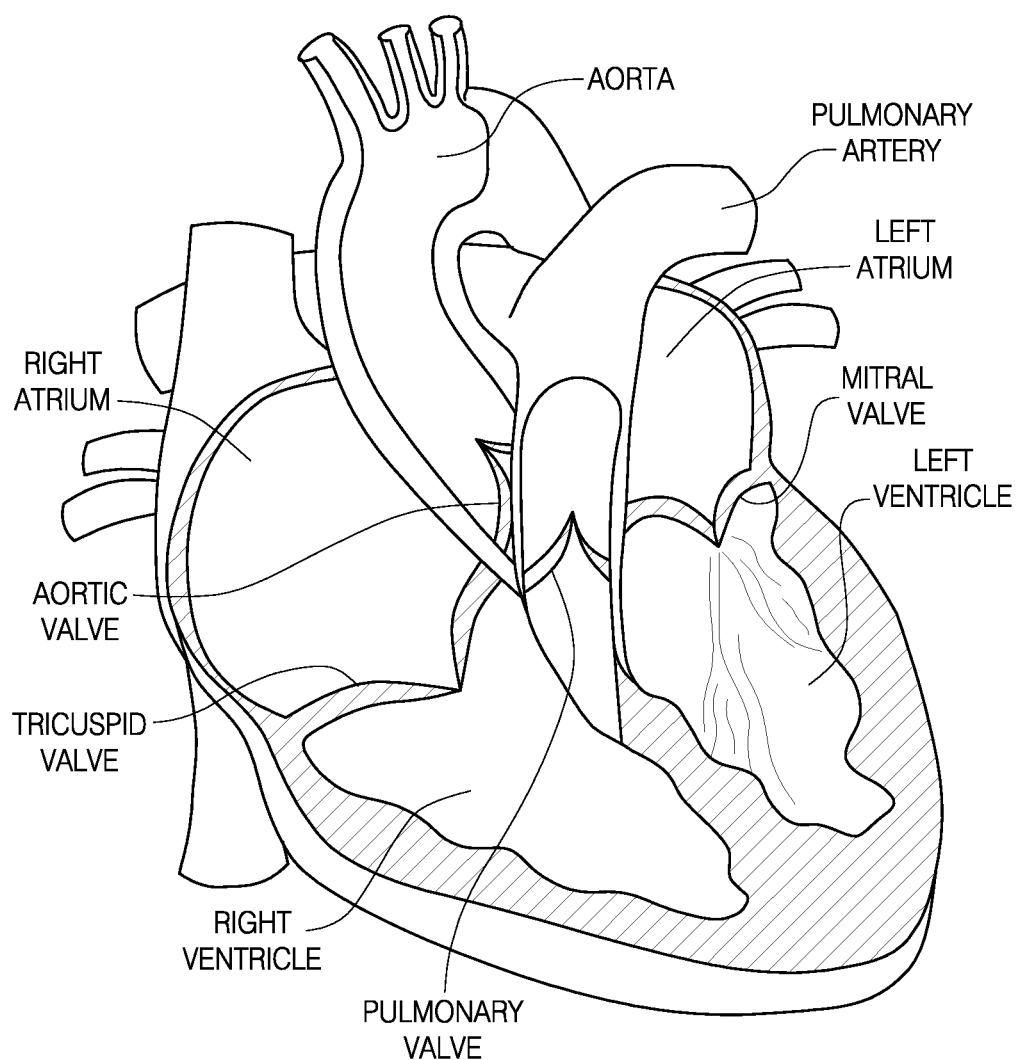
FIG. 1 shows a schematic cross-sectional view of a human heart.
Figure 2:
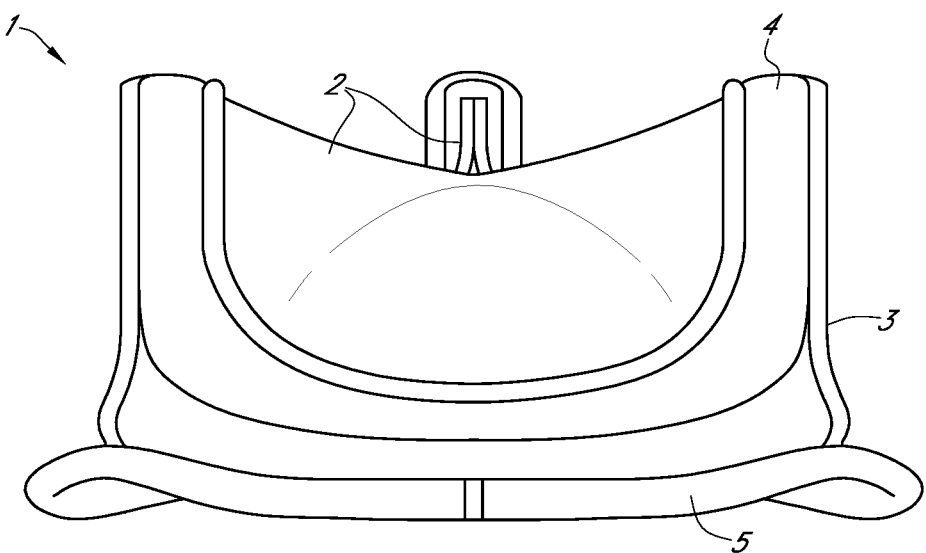
FIG. 2 shows a schematic perspective view of an example of a prosthetic valve that can be used with some embodiments.
Figure 3A:
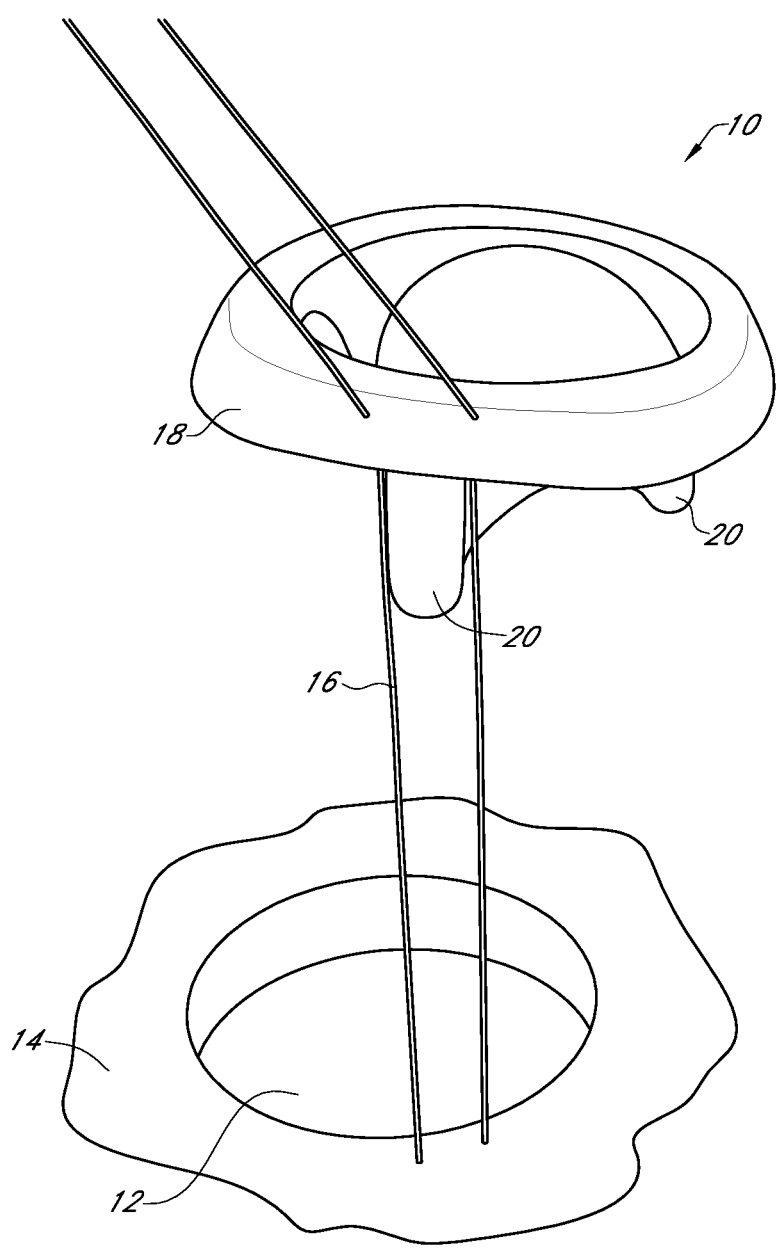
FIG. 3A is a schematic view of a prosthetic heart valve as it is parachuted to a mitral valve opening.
Figure 3B:
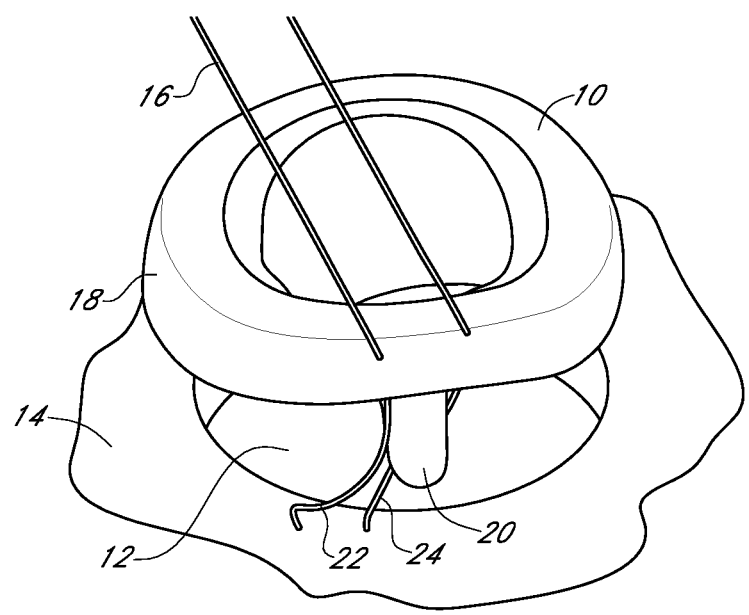
FIG. 3B is a schematic view of the prosthetic heart valve of FIG. 3A just before entering the mitral valve opening.
Figure 3C:
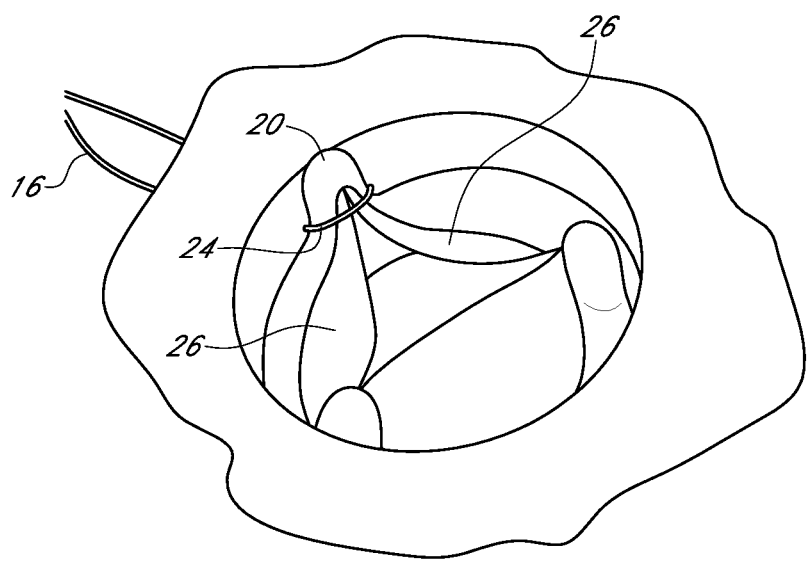
FIG. 3C is a schematic view of the prosthetic heart valve of FIG. 3A after entering the mitral valve opening, as shown from the opposite side of the mitral valve opening.
Figure 4:
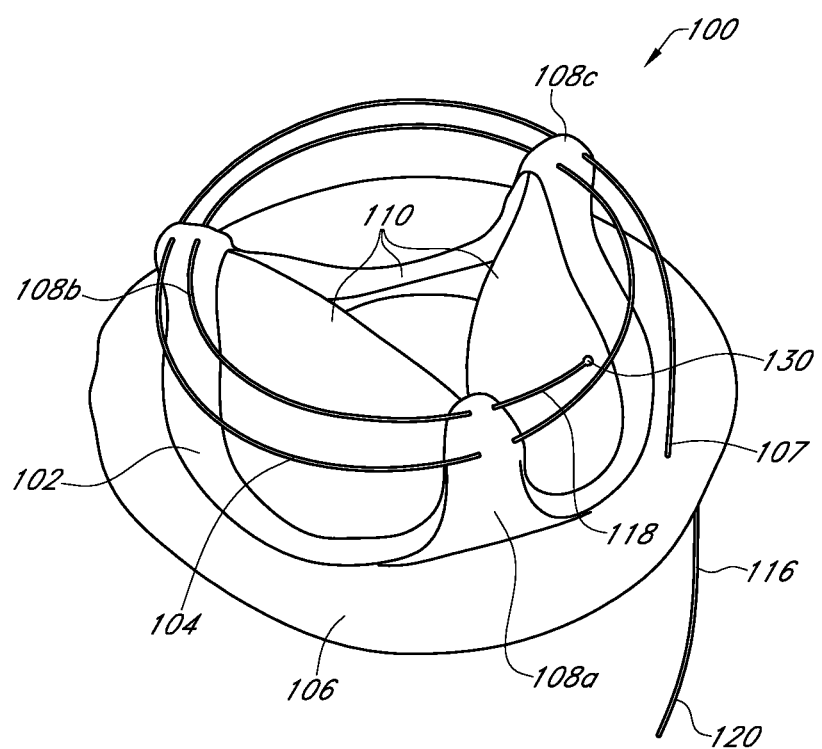
FIG. 4 is a prosthetic heart valve with an anti-loop member according to an embodiment.

With reference to FIG. 4, a prosthetic heart valve system 100 includes a prosthetic heart valve 102 and an anti-loop member 104. The heart valve 102 has a base including an annular sewing ring 106 on an inflow side, and a plurality of commissure posts 108a, 108b, 108c projecting generally axially in the outflow direction. The inflow side of the valve 102 is the proximal (e.g., accessible) side during implantation and the commissure posts 108 project distally toward the outflow side of the valve 102, defining the leading end of the valve during implantation.

The heart valve 102 further includes a plurality of flexible leaflets 110 that are supported by and extend between the commissure posts 108. The leaflets 110 provide the occluding surfaces of the valve 102, and may be made of individual pieces of bovine pericardium, for example. Alternatively, the leaflets 110 may be part of an entire xenograft, or homograft. In the former instance, natural porcine (pig) valves are particularly useful. Therefore it should be understood that the leaflets 110 may be formed of a variety of materials, none of which is limiting with respect to the present disclosure. In addition, there are preferably three such leaflets 110 corresponding to the three commissure posts 108.

Various constructions for the heart valve 102 are known, which may include metallic or plastic stent elements, a silicone or urethane insert for the sewing ring 106, biocompatible fabric or cloth (e.g., polyester) covering around one or more of the elements. In a preferred embodiment, the heart valve 102 includes an internal metallic wireform (not shown) having an undulating shape with a plurality of arcuate cusps connected by the upstanding commissures. The wireform commissures provide internal structure for the commissure posts 108 of the valve, and are somewhat flexible so as to be able to flex or cantilever inward.

The anti-loop member 104 is preferably a fine guide wire made of a flexible material such as a superelastic nitinol or other suitable material. Preferably, the guide wire is in the form of a coil and the material is such that the coil is not permanently bent or deformed after coiling. This permits the coil to be passed through the commissure tips during assembly without permanently deforming and permits easy removal from the commissure posts without pulling on the cloth and damaging the heart valve. In addition, the coil material is preferably rigid enough to retain its shape when coming in contact with sutures used to secure the heart valve to the heart valve annulus to prevent suture looping. In a preferred embodiment, the coil is shape set in a circular or otherwise coiled form before attaching it to the commissure tips so that the free end does not stick out of the coil at the outflow side.

The anti-loop member 104 has a first end portion 116 and a second end portion 118. The anti-loop member 104 is assembled to the prosthetic heart valve 102 by taking the free end 120 of the first end portion 116 and passing it through the covering or an attached loop (such as by a suture) at the tip of the first commissure post 108a, then through the covering or loop at the tip of the second commissure post 108b and through the covering or loop at the tip of the third commissure post 108c. Preferably, the free end 120 continues to be fed to the first commissure post 108a such that the anti-loop member 104 extends from the first commissure post 108 around the periphery of the heart valve to the second and third commissure posts 108b, 108c and back to the first commissure 108a. If desired, the free end 120 of the first end portion 116 can continue to be passed through the commissures posts 108b, 108c consecutively. In the embodiment of FIG. 4, the anti-loop member passed through each commissure post twice before being passed through the sewing ring 106 to be engaged by a forceps (or other means) for removal after the heart valve has been placed or secured on the valve annulus. Preferably, the anti-loop member 104 passes through the sewing ring 106 at an inner diameter portion 107 of the sewing ring. This will permit easier removal of the anti-loop member after the heart valve is seated on the valve annulus.

If the anti-loop member is coiled around the commissures twice, the inner coil may be attached on an inner side of the commissure posts while the outer coil may be on an outer side of the commissure posts. Alternatively, the coils may be adjacent each other, both on the outside, both on the inside, or other variations. It will be appreciated that the anti-loop member 104 can be assembled to the heart valve in the opposite direction also (e.g., through the sewing ring 6 first, then through the commissure posts.

To prevent the free end of the second end portion 118 of the coil from scratching or damaging surrounding tissue, a small ball 130, or other shape of protector, can be attached to it. The ball is small enough so that it does not impede pulling the coil through the commissures. A plastic ball can be molded onto the free end of the coil. Alternatively, a metal ball may be formed by melting the free end of the coil so that nothing may fall off the free end. Other shapes may be used as long as the shape not only prevents the coil's free end from poking into the surrounding heart tissue but also does not impede pulling the coil through its attachment points on the commissures.

With reference to FIGS. 5A-5D, the prosthetic heart valve 102 is shown in a sequence of views as it is parachuting to a valve opening 140 of the human heart. As is well known in the art, several sutures are passed through a valve annulus 142 and through the sewing ring 106. Only one suture 144 is shown for clarity.

Figure 5A:
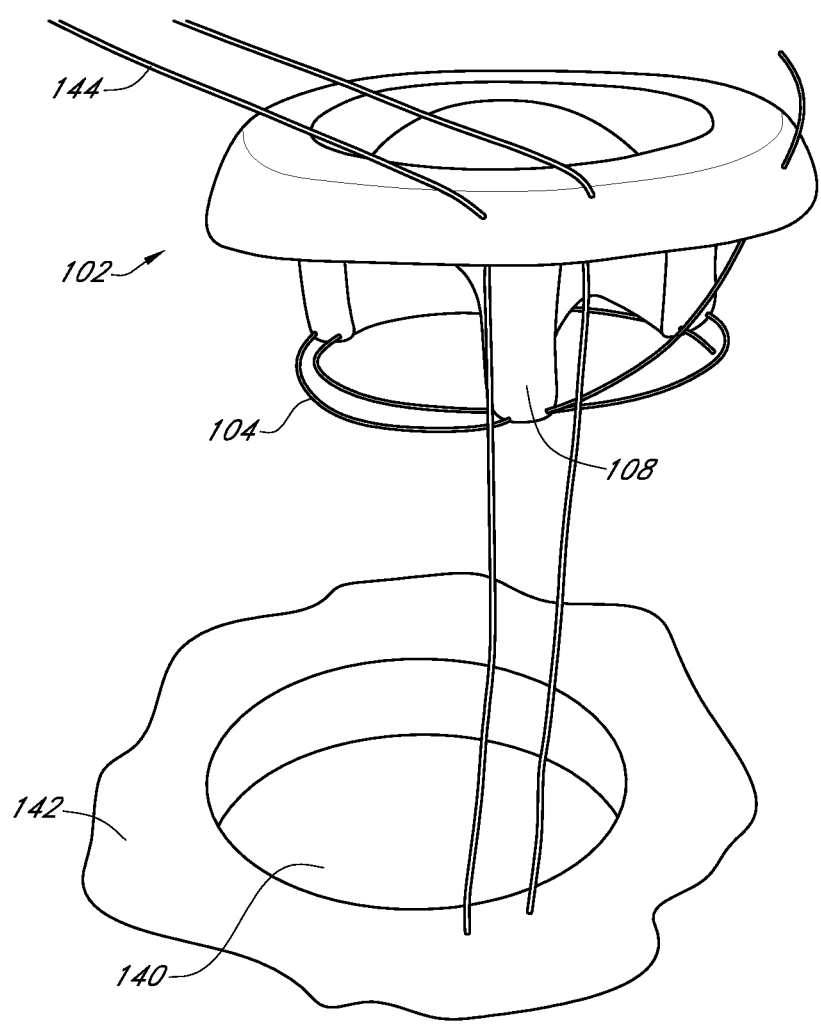
FIGS. 5A-5C are a sequence of views showing the prosthetic heart valve and anti-loop member of FIG. 4 as it is parachuted to a valve opening.
Figure 5B:
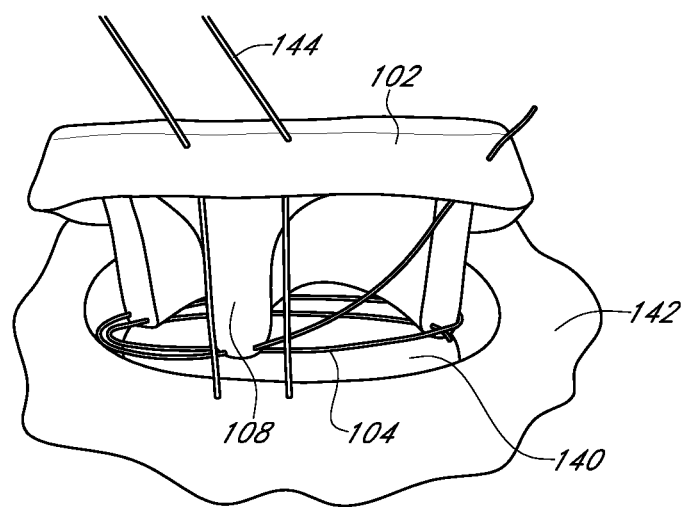
Figure 5C:
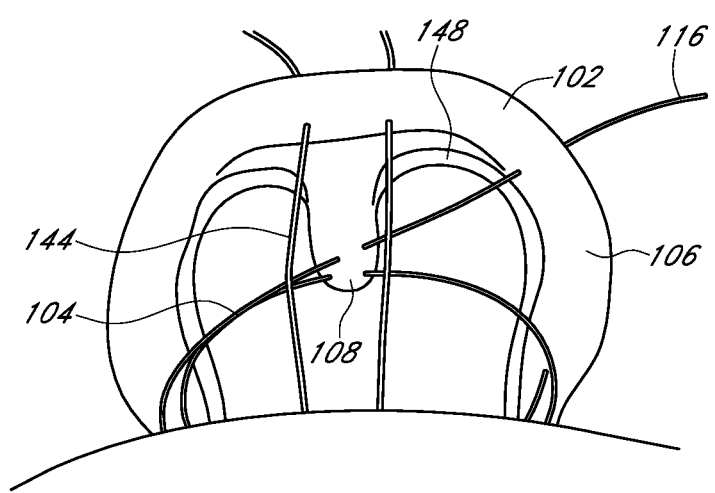
Figure 5D:
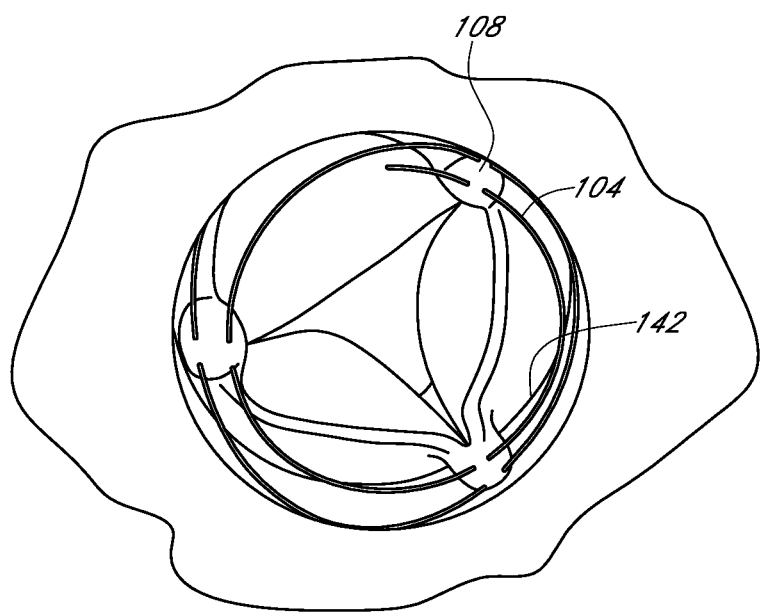
FIG. 5D is a view of the prosthetic heart valve and anti-loop member of FIG. 4 after entering the valve opening, as shown from the opposite side of the valve opening.
Figure 6A:
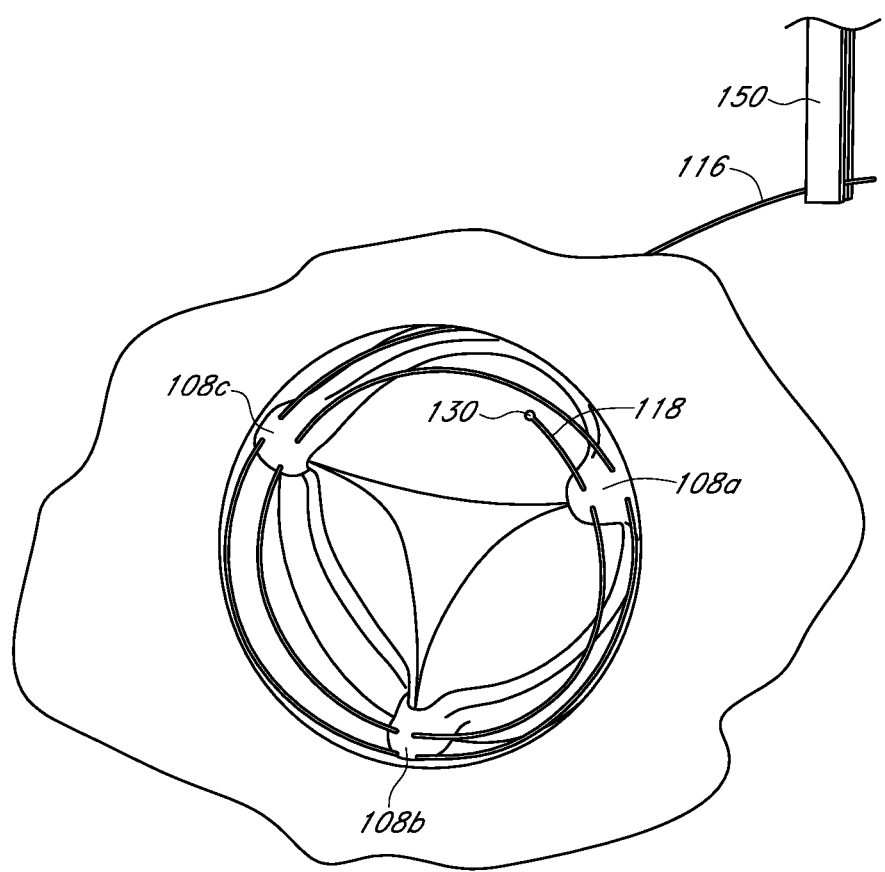
FIGS. 6A-6E are a sequence of views showing removal of the anti-loop member from the prosthetic heart valve of FIG. 4 as shown from the opposite side of the valve opening.
Figure 6B:
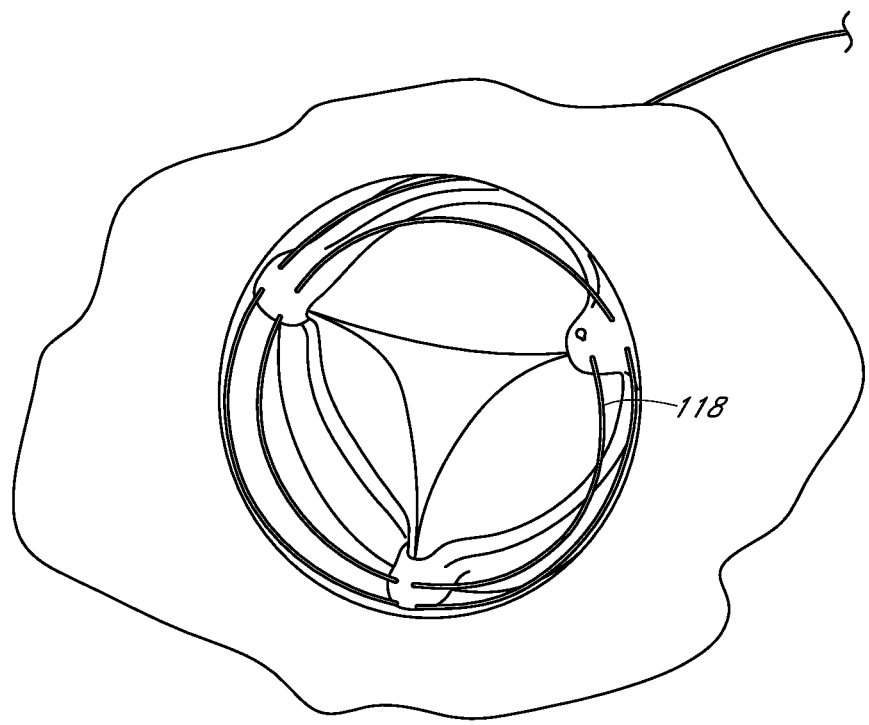
Figure 6C:
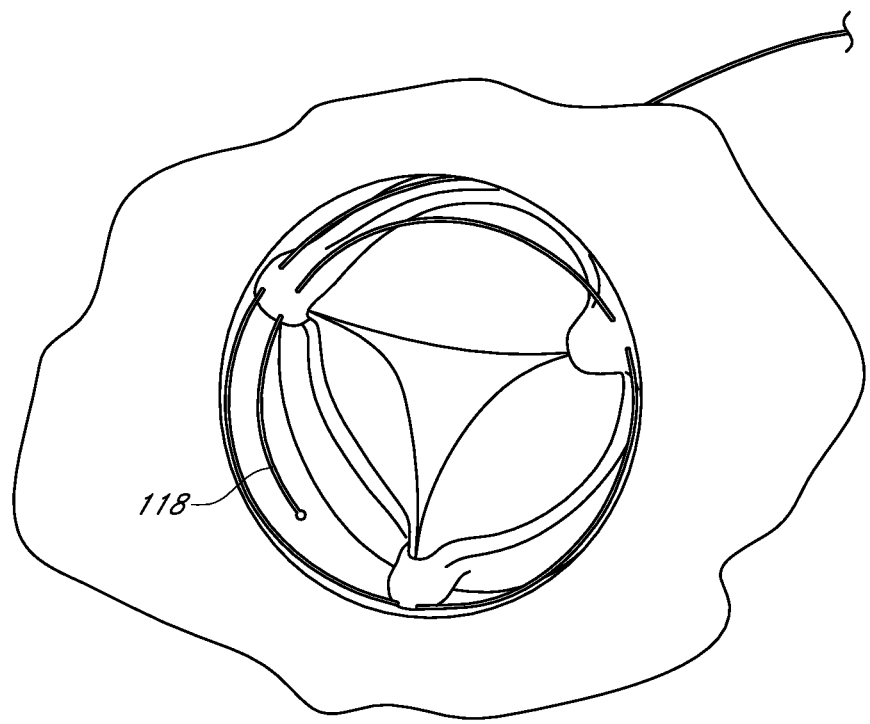
Figure 6D:
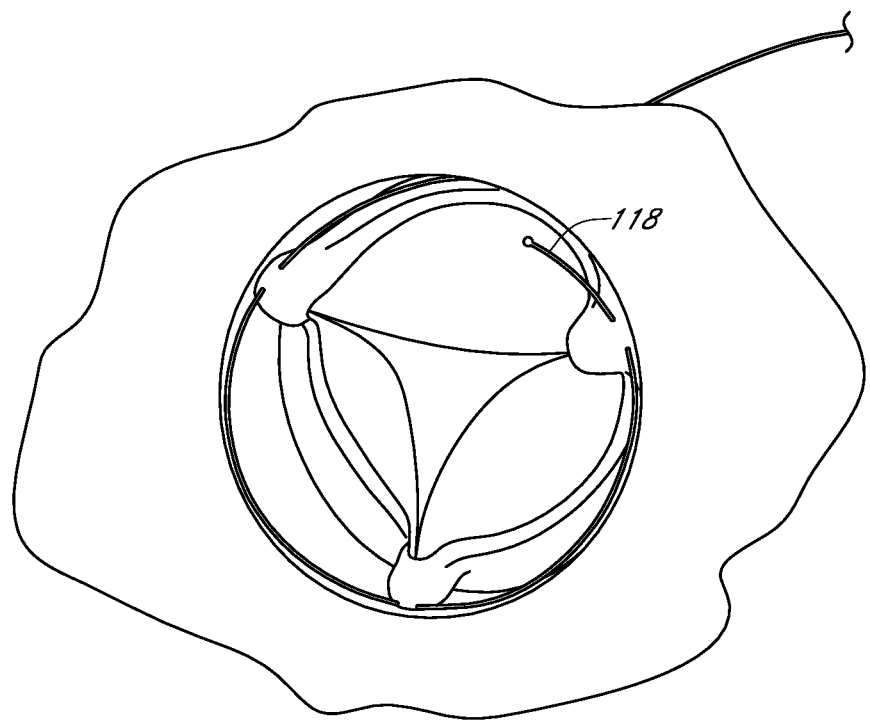
Figure 6E:
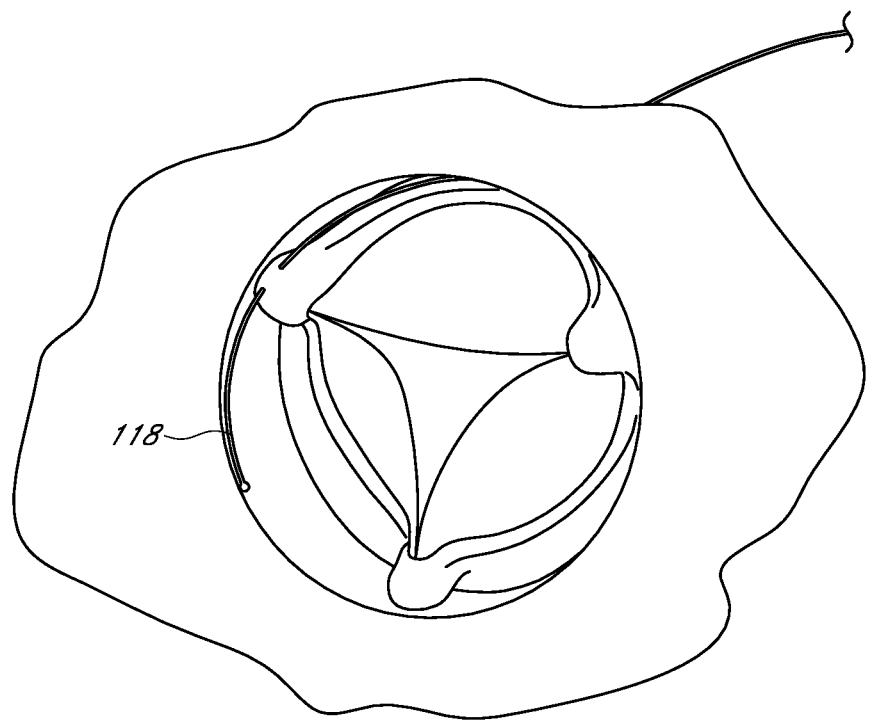

As the heart valve 102 is parachuted to the valve annulus 142 (FIG. 5A), it is seen that the anti-loop member 104 is in position to deflect the suture 144 to a location outside the commissure posts 108 to prevent suture looping (FIG. 5B). Tilting of the heart valve 102 for easier entry into the valve opening can also be safely achieved without suture looping due to the location of the anti-loop member 104 (FIG. 5C). The suture 144 is deflected by the anti-loop member 104 to prevent it from looping inside the commissure post 108. Once the heart valve 102 is fully seated against the valve annulus 142 (FIG. 5D, viewed from the opposite side of the valve opening), the surgeon is able to view the valve seating through the valve leaflets before and during tying of the suture knots. The presence of the anti-loop member 104 also prevents suture looping as the suture knots are being tied.

Once the heart valve 102 is sufficiently secured to the valve annulus 142, the anti-loop member 104 can be removed. In one embodiment (see FIG. 5C), the first end portion 116 of the anti-loop member 104 passes through the sewing ring 106 at a location next to a low point 148 of a cusp of one of the commissures 108. Having the first end portion exit through the sewing ring at a distance away from the last commissure will reduce stress on the commissure during removal of the anti-loop member.

With reference to FIGS. 6A-6E, a surgeon may grasp the first end portion 116 of the anti-loop member 104 with a forceps 150 at the inflow side of the valve annulus. Pulling on the anti-loop member will cause the second end portion 118 to unwind through the commissure posts 108 on the outflow side of the heart valve, and finally through the sewing ring 106, releasing the anti-loop member from the heart valve. The first end portion of the anti-loop member can be provided with an indicator to alert the surgeon to grab the end of the coil. The indicator can be in vivid colors or other eye-catching device to contrast it from the environment to prevent it from being left behind after completion of valve implantation.

Figure 7:
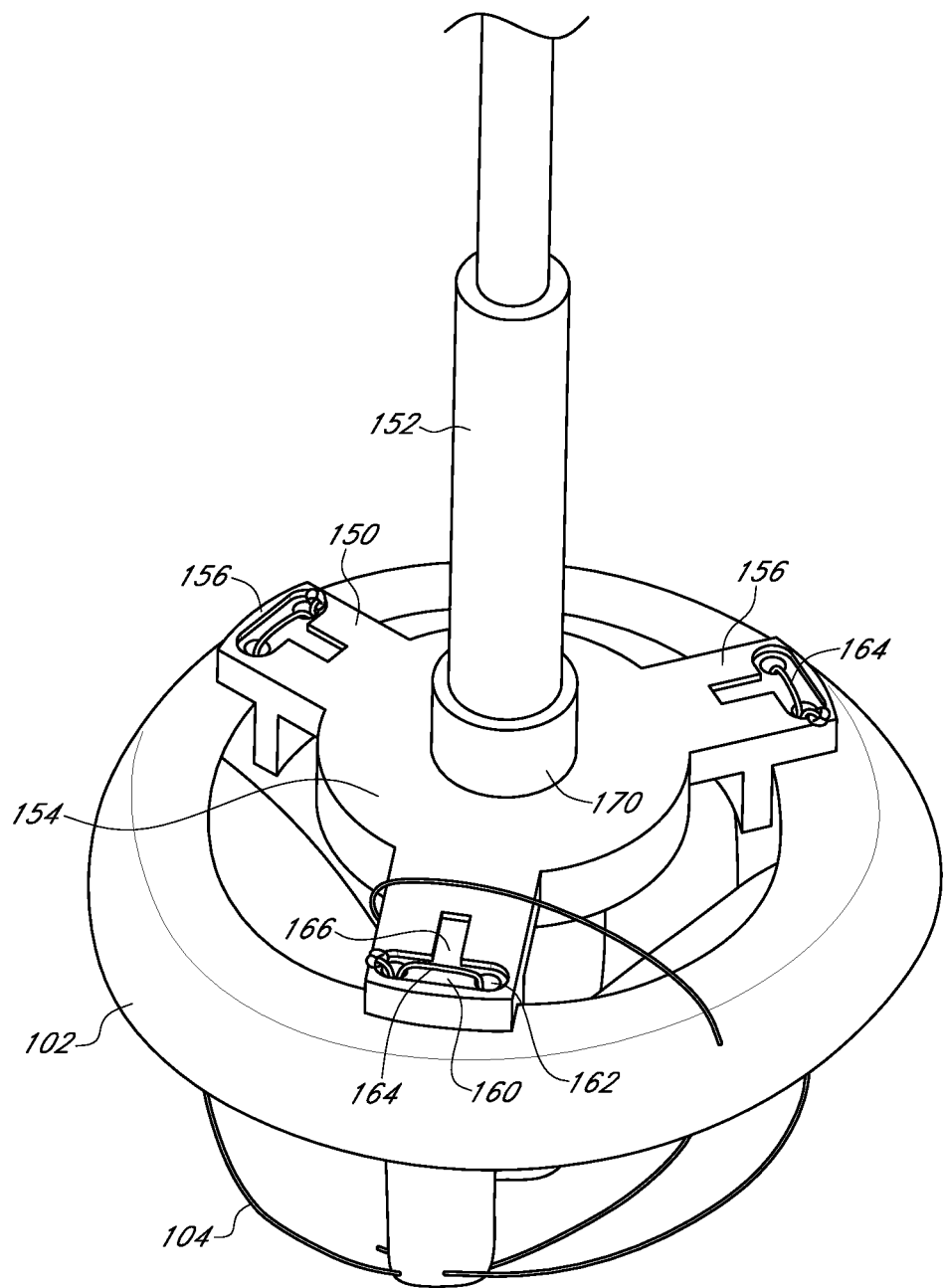
FIG. 7 is a perspective view of the heart valve and anti-loop member of FIG. 4 attached to a holder.

In a further embodiment, the prosthetic heart valve system includes a valve holder and a handle. With reference to FIG. 7, the prosthetic heart valve 102 and anti-loop member 104 are secured to a valve holder 150 and a handle 152. The holder includes a central disk portion 154 and three arms 156 equally spaced around and extending away from the disk portion 154. Each arm 156 has a free end portion and a recess 160 provided in a top side of the free end portion. In the recess 160 is a pair of holes 162 through the arm to permit attachment of the holder to the heart valve 102 by a suture 164 passing through the holes. The recess also extends axially and has a deeper portion 166 to permit access for a cutting tool for cutting the suture.

The holder also includes a central post 170 that protrudes axially in a proximal direction. The central post 170 has a threaded opening (not shown) to receive the handle 152, which also has cooperative threading for attaching the handle to the valve holder. The first end portion 116 of the anti-loop member 104 is optionally connected to the holder, e.g., by tying down to an arm 156 of the holder 150. Alternatively, the arm can be molded onto the free end of the coil, or other suitable means to secure the coil 104 to the holder 150.

As will be appreciated, the holder 150 can be removed from the heart valve by cutting the sutures 164. The sutures are tied to the holder and will be removed with the holder. Similarly, in this embodiment, the anti-loop member 104 is connected to the holder and will be removed with the holder. Alternatively, the anti-loop member is not connected to the holder and can be removed separately. After the heart valve is placed on the native valve annulus, the holder can be removed and the surgeon is provided a clear view to check on valve seating before and during tying of the suture knots, even when the anti-loop member is still present. The presence of the coil will prevent suture looping during the knot tying procedure. After all the suture knots are tied, the surgeon can easily pull the anti-loop member out by grabbing on the first end of the member.

In other alternative embodiments, various different features from the different embodiments discussed above can also be combined in a single modified ring holder.

For purposes of this description, certain aspects, advantages, and novel features of the embodiments of this disclosure are described herein. The disclosed methods, apparatus, and systems should not be construed as being limiting in any way. Instead, the present disclosure is directed toward all features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A prosthetic heart valve system, comprising:
   a prosthetic heart valve having an inflow side and an outflow side, and a flow axis therethrough, the heart valve further comprising a base at the inflow side, a plurality of commissure posts extending from the base away from the inflow side and circumferentially spaced around the flow axis, and valve leaflets secured to the commissure posts to permit flow through the heart valve, each commissure post having a tip on the outflow side; and
   an anti-loop member having a first portion and a second portion, the first portion of the anti-loop member on the inflow side of the heart valve and the second portion of the anti-loop member on the outflow side of the heart valve; the second portion of the anti-loop member arranged to pass in a coiled form through a covering of fabric or cloth or an attached loop extending from the covering at the tip of each commissure post, and engaging at least one commissure post twice to form a coiled loop around all of the plurality of commissure posts, wherein the anti-loop member is a superelastic nitinol wire shape set in a coiled form, and wherein the second portion when assembled with the heart valve to prevent suture looping terminates in a free end located at the outflow side that is within and does not extend radially outward from the coiled loop, and wherein the coiled loop may be disengaged from the commissure post tips to release the anti-loop member from the heart valve by simply pulling on the first portion;
   wherein the anti-loop member comprises a material sufficiently flexible to be removed from the commissure posts without damaging the heart valve by pulling on the first end portion of the anti-loop member yet rigid enough to retain its shape when coming in contact with sutures used to secure the heart valve to a heart valve annulus.

2. The prosthetic heart valve system of claim 1, wherein the plurality of commissure posts is three or more commissure posts.

3. The prosthetic heart valve system of claim 1, wherein the anti-loop member is attached to a side of each commissure post facing away from the flow axis.

4. The prosthetic heart valve system of claim 1, wherein the anti-loop member loops around the plurality of commissure posts twice.

5. The prosthetic heart valve system of claim 4, wherein an outer loop of the anti-loop member is attached to a side of each commissure post facing away from the flow axis and an inner loop of the anti-loop member is inside the outer loop.

6. The prosthetic heart valve system of claim 1, further including a valve holder removably secured to the prosthetic heart valve wherein the first portion of the anti-loop member is secured to the valve holder such that removal of the valve holder from the heart valve also results in removal of the anti-loop member from the heart valve.

7. The prosthetic heart valve system of claim 6, wherein the valve holder has a central portion and three arms equally spaced around and extending away from the central portion, and the first portion of the anti-loop member is secured to one of the arms.

8. The prosthetic heart valve system of claim 1, wherein the free end of the second portion of the anti-loop member is located radially inside the periphery of the plurality of commissure posts.

9. The prosthetic heart valve system of claim 1, wherein the free end of the second portion of the anti-loop member is an enlarged portion shaped to prevent damage to surrounding tissue.

10. The prosthetic heart valve system of claim 9, wherein the enlarged portion is in the shape of a ball.

11. The prosthetic heart valve system of claim 1, wherein the base of the prosthetic heart valve comprises a sewing ring to engage a native valve annulus and the anti-loop member passes through the sewing ring.

12. The prosthetic heart valve system of claim 11, wherein the anti-loop member passes through the sewing ring adjacent an inner diameter of the sewing ring.

13. The prosthetic heart valve system of claim 12, wherein the anti-loop member extends from a tip of one commissure post and through the sewing ring at a location closer to an adjacent commissure post than the one commissure post.

14. A prosthetic heart valve system, comprising:
   a prosthetic heart valve having an inflow side and an outflow side, and a flow axis therethrough, the heart valve further comprising a base at the inflow side, a plurality of commissure posts extending from the base away from the inflow side and circumferentially spaced around the flow axis, and valve leaflets secured to the commissure posts to permit flow through the heart valve, each commissure post having a tip on the outflow side;
   an anti-loop member having a first portion and a second portion, the first portion of the anti-loop member on the inflow side of the heart valve and the second portion of the anti-loop member on the outflow side of the heart valve; the second portion of the anti-loop member arranged to pass in a coiled form through a covering of fabric or cloth or an attached loop extending from the covering at the tip of each commissure post, and engaging at least one commissure post twice to form a coiled loop around all of the plurality of commissure posts, wherein the anti-loop member is a superelastic nitinol wire shape set in a coiled form, and wherein the second portion when assembled with the heart valve to prevent suture looping terminates in a free end located at the outflow side that is within and does not extend radially outward from the coiled loop, and wherein the coiled loop may be disengaged from the commissure post tips to release the anti-loop member from the heart valve by simply pulling on the first portion; and a valve holder removably secured to the prosthetic heart valve;

wherein the anti-loop member comprises a material sufficiently flexible to be removed from the commissure posts without damaging the heart valve by pulling on the first end portion of the anti-loop member yet rigid enough to retain its shape when coming in contact with sutures used to secure the heart valve to a heart valve annulus.

15. The prosthetic heart valve system of claim 14, wherein the first portion of the anti-loop member is secured to the valve holder such that removal of the valve holder from the heart valve also results in removal of the anti-loop member from the heart valve.

16. The prosthetic heart valve system of claim 14, wherein the valve holder is secured to the prosthetic heart valve by sutures.

17. The prosthetic heart valve system of claim 14, further comprising a handle removably attachable to the valve holder.

18. The prosthetic heart valve system of claim 14, wherein the first portion of the anti-loop member comprises an indicator to alert a member of the surgical team to remove the anti-loop coil.

19. The prosthetic heart valve system of claim 18, wherein the indicator is a contrasting color to a surrounding native environment when the heart valve is implanted.

20. The prosthetic heart valve system of claim 14, wherein the free end of the second portion of the anti-loop member is an enlarged portion in the shape of a ball to prevent damage to surrounding tissue.

* * * * *